(12) United States Patent
Huang et al.

(10) Patent No.: US 10,358,398 B2
(45) Date of Patent: Jul. 23, 2019

(54) DEHYDROGENATION OF PROPANE USING A METAL-CONTAINING CATALYST ON A SUPPORT

(71) Applicant: Iowa State University Research Foundation, Inc., Ames, IA (US)

(72) Inventors: Wenyu Huang, Ames, IA (US); Chaoxian Xiao, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 15/596,800

(22) Filed: May 16, 2017

(65) Prior Publication Data

US 2017/0334808 A1 Nov. 23, 2017

Related U.S. Application Data

(60) Provisional application No. 62/337,715, filed on May 17, 2016.

(51) Int. Cl.
*B01J 37/18* (2006.01)
*C07C 5/333* (2006.01)
(Continued)

(52) U.S. Cl.
CPC ............ *C07C 5/3337* (2013.01); *B01J 23/42* (2013.01); *B01J 23/626* (2013.01); *B01J 35/002* (2013.01);
(Continued)

(58) Field of Classification Search
CPC ... B01J 21/08; B01J 23/02; B01J 23/06; B01J 23/08; B01J 23/16; B01J 23/38;
(Continued)

(56) References Cited

U.S. PATENT DOCUMENTS 2,349,904 A * 5/1944 Hachmuth ............... B01J 21/12
34/329
2,890,178 A * 6/1959 Thorn ...................... B01J 23/40
502/230
(Continued)

FOREIGN PATENT DOCUMENTS

| CN | 103785388 A | 5/2014 |
|----|-------------|--------|
| CN | 104248968 A | 12/2014 |
| CN | 104289219 A | 1/2015 |

OTHER PUBLICATIONS

Bariås et al., Propane Dehydrogenation over Supported Pt and Pt—Sn Catalysts: Catalyst Preparation, Characterization, and Activity Measurements, J. Catalysis 158(1):1-12 (1996).
(Continued)

*Primary Examiner* — Patricia L. Hailey
(74) *Attorney, Agent, or Firm* — Pepper Hamilton LLP

(57) ABSTRACT

The present invention relates to a process of producing a metal-containing catalyst. The process involves mixing a support material with one or more metals in a solution to produce a catalyst comprising a metal-loaded support. The catalyst comprising a metal-loaded support is treated with an atmosphere comprising 0.01 to 100% carbon-containing agents and 0-100% hydrogen at a temperature of 50 to 500° C. to produce a treated metal-containing catalyst on a support. Also disclosed is the resulting treated metal-containing catalyst and its use in a process for converting propane to propylene.

2 Claims, 7 Drawing Sheets

(51) Int. Cl.
*B01J 23/42* (2006.01)
*B01J 23/62* (2006.01)
*B01J 37/08* (2006.01)
*B01J 35/00* (2006.01)
*B01J 21/08* (2006.01)
*B01J 23/02* (2006.01)
*B01J 23/06* (2006.01)
*B01J 23/08* (2006.01)
*B01J 23/16* (2006.01)
*B01J 23/38* (2006.01)
*B01J 23/70* (2006.01)
*B01J 37/02* (2006.01)
*B01J 37/04* (2006.01)
*B01J 37/16* (2006.01)

(52) U.S. Cl.
CPC ............... *B01J 37/08* (2013.01); *B01J 37/18* (2013.01); *C07C 2523/42* (2013.01); *C07C 2523/62* (2013.01); *C07C 2529/74* (2013.01); *Y02P 20/52* (2015.11)

(58) Field of Classification Search
CPC ... B01J 23/70; B01J 37/02; B01J 37/04; B01J 37/16; B01J 37/18; B01J 23/622
USPC .................. 502/240, 242–248, 250–263, 339
See application file for complete search history.

(56) References Cited

U.S. PATENT DOCUMENTS

| | | | | | |
|---|---|---|---|---|---|
| 2,917,565 | A | * | 12/1959 | Carr | B01J 23/755 208/135 |
| 2,967,207 | A | * | 1/1961 | Miller | B01J 23/89 502/259 |
| 3,274,286 | A | * | 9/1966 | Reich | B01J 23/76 502/245 |
| 3,759,841 | A | * | 9/1973 | Wilhelm | B01J 23/622 208/138 |
| 3,821,323 | A | * | 6/1974 | Schulze | B01J 23/60 585/261 |
| 4,087,352 | A | * | 5/1978 | Antos | B01J 23/622 208/139 |
| 4,093,559 | A | * | 6/1978 | Fernholz | B01J 23/44 502/170 |
| 5,051,384 | A | * | 9/1991 | Robbins | B01J 29/068 502/241 |
| 5,128,300 | A | * | 7/1992 | Chao | B01J 23/622 502/227 |
| 5,137,620 | A | * | 8/1992 | Robbins | B01J 23/40 208/134 |
| 5,877,369 | A | * | 3/1999 | Wu | B01J 23/18 502/325 |
| 6,818,582 | B2 | * | 11/2004 | Maunula | B01D 53/9422 502/73 |
| 8,362,306 | B2 | | 1/2013 | Wheeler et al. | |
| 2001/0016555 | A1 | * | 8/2001 | Zhang | B01J 23/58 502/325 |

OTHER PUBLICATIONS

Case et al., "Liquid Hydrocarbon Fuels From Cellulosic Feedstocks via Thermal Deoxygenation of Levulinic Acid and Formic Acid Salt Mixtures," Green Chemistry 14(1):85-89 (2012).

Deng et al., "Dehydrogenation of Propane over Silica-Supported Platinum-Tin Catalysts Prepared by Direct Reduction: Effects of Tin/Platinum Ratio and Reduction Temperature," Chem. Cat. Chem. 6(9):2680-2691 (2014).

Fan et al., "Dehydrogenation of Propane Over PtSnAl/SBA-15 Catalysts: Al Addition Effect and Coke Formation Analysis," Catal. Sci. Technol. 5(1):339-350 (2015).

Humbolt et al., "Surface Organometallic Chemistry on Metals: Selective Dehydrogenation of Isobutane into Isobutene on Bimetallic Catalysts Prepared by Reaction of Tetran-Butyltin on Silica-Supported Platinum Catalyst," J. Catalysis 179(2):459-468 (1998).

Schwartz et al., "Energy Densification of Levulinic Acid by Thermal Deoxygenation," Green Chemistry 12(8):1353-1356 (2010).

Yarusov et al., "Propane Dehydrogenation Over Pt—Sn Catalysts," Catalysis Today 13(4):655-658 (1992).

Zhu et al., "Sn Surface-Enriched Pt—Sn Bimetallic Nanoparticles as a Selective and Stable Catalyst for Propane Dehydrogenation," J. Catalysis 320:52-62 (2014).

* cited by examiner

DEHYDROGENATION OF PROPANE USING A METAL-CONTAINING CATALYST ON A SUPPORT

This application claims the benefit of U.S. Provisional Patent Application Ser. No. 62/337,715 filed May 17, 2016, which is hereby incorporated by reference in its entirety.

FIELD OF THE INVENTION

The present invention relates to dehydrogenation of propane using a metal-containing catalyst on a support.

BACKGROUND OF THE INVENTION

Propylene is an important commodity chemical, widely used to produce plastics, rubbers, fibers, and films. Propylene is also used in the production of polypropylene, acrylonitrile, and propylene oxide. In 2013 alone, approximately 85 million tons of propylene was processed worldwide.

Propylene is commonly produced as a byproduct during the steam cracking of naphtha and oil and during the fluid catalytic cracking used to produce gasoline and ethylene. As the commercial demand for propylene increases, maximizing the yield of propane has become increasingly desirable. In particular, propylene can be generated through the catalytic dehydrogenation of propane, which is one of the major components of natural gas (shale gas) or liquefied petroleum gas.

The dehydrogenation of propane to propylene is a highly endothermic process, often requiring high temperatures and the use of a catalyst. Major catalysts used in the industry for catalytic dehydrogenation of propane include alumina-supported platinum-tin based catalysts. Such catalysts are both highly active and selective, but are susceptible to coke deposition and deactivation during catalysis. Use of such alumina-supported platinum-tin catalysts requires frequent regeneration to recover catalytic activity, which increases off time during the dehydrogenation reaction.

U.S. Pat. No. 3,978,150 discloses a continuous process for the dehydrogenation of propane to minimize reactor downtime. This technology utilizes a complicated cyclone reactor design to allow the continuous removal of deactivated catalyst from the reactor and continuous regeneration and feeding into the reactor, which could increase capital and operation costs. Additionally, this process does not improve the stability of the catalyst, which is highly desired.

The disclosure herein is directed to overcoming these and other deficiencies in the art.

SUMMARY OF THE INVENTION

The present invention relates to a process of producing a metal-containing catalyst. The process involves mixing a support material with one or more metals in a solution to produce a catalyst comprising a metal-loaded support. The catalyst comprising a metal-loaded support is treated with an atmosphere comprising 0.01 to 100% carbon-containing agents and 0-100% hydrogen at a temperature of 50 to 500° C. to produce a treated metal-containing catalyst on a support.

The present invention also relates to a catalytic agent, which comprises a support material and a platinum-containing catalyst supported on the support material. The platinum-containing catalyst is stable for 40-1000 hours at conditions suitable for the catalytic agent to convert propane to propylene.

The present invention further describes a process for converting propane to propylene. The process involves converting propane to propylene in the presence of the treated platinum-tin catalyst of the present invention.

The present invention also discloses a process for converting propane to propylene. The process involves providing a platinum-containing catalyst on a support material; treating the platinum-containing catalyst on a support material with an atmosphere comprising 0.01 to 100% carbon-containing agents and 0-100% hydrogen at a temperature of 50 to 500° C. to produce a treated platinum-containing catalyst on a support material; and converting propane to propylene in the presence of the treated platinum-containing catalyst on a support.

The treatment of the present invention significantly enhances the stability of the catalyst. Catalysts prepared according to this method showed unprecedented stability during long-term runs (>400 hours) and high selectivity to propylene (>99%) at a good conversion (~27%). The high selectivity and improved stability of the treated catalyst can minimize the consumption of propane feedstock (which accounts for approximately 60% of operational costs) and decrease reaction downtime (which would reduce operational costs).

DETAILED DESCRIPTION OF THE INVENTION

Figure 1:
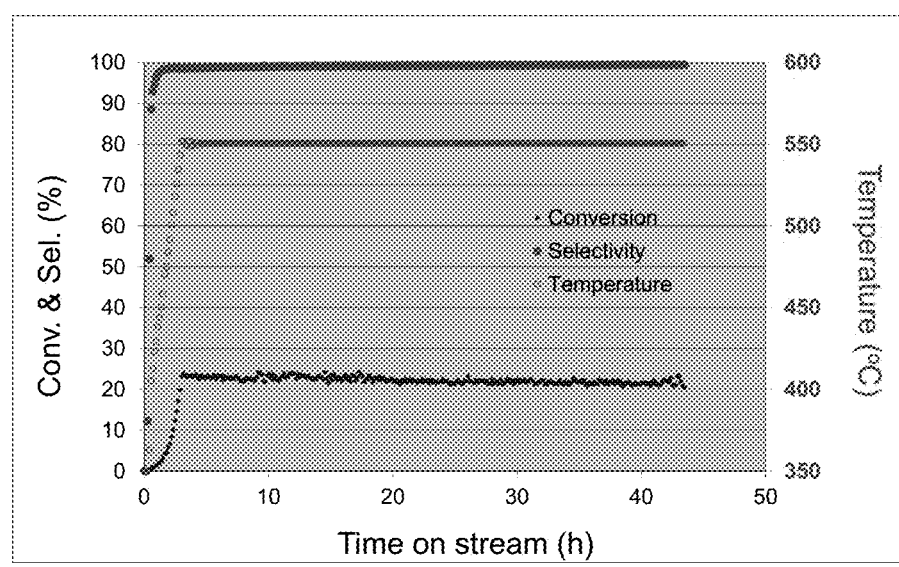
FIG. 1 is a graph showing the conversion and selectivity of the catalytic dehydrogenation of propane to propylene using a 1% $PtSn/SiO_2$ catalyst treated with ethylene and acetylene at 240° C. The graph shows time dependent performance of the 1% $PtSn/SiO_2$ catalyst when the reaction gases were composed of $He/H_2/C_3H_8$=5.6/2.8/2.8 mL/min.

The present invention relates to a process of producing a metal-containing catalyst. The process involves mixing a support material with one or more metals in a solution to produce a catalyst comprising a metal-loaded support. The catalyst comprising a metal-loaded support is treated with an atmosphere comprising 0.01 to 100% carbon-containing agents and 0-100% hydrogen at a temperature of 50 to 500° C. to produce a treated metal-containing catalyst on a support.

The one or more metals may be selected from the group consisting of platinum (Pt), palladium (Pd), ruthenium (Ru), iron (Fe), cobalt (Co), nickel (Ni), copper (Cu), molybdenum (Mo), vanadium (V), tin (Sn), indium (In), gallium (Ga), zinc (Zn), lithium (Li), sodium (Na), potassium (K), rubidium (Rb), cesium (Cs), magnesium (Mg), calcium (Ca), strontium (Sr), and barium (Ba).

The solution may be an aqueous solution or an acetone solution.

As used herein, the term "aqueous solution" refers to a solution in which the solvent is water. In certain embodiments the aqueous solution comprises deionized water, or water prepared by reverse osmosis.

The aqueous solution may comprise a platinum compound including, but not limited to platinum chloride, chloroplatinic acid, ammonium chloroplatinate, dinitrodiamino platinum, palladium chloride, and chloropalladic acid. In one embodiment, the platinum compound is chloroplatinic acid. In another embodiment, the platinum compound is chloroplatinic acid hexahydrate.

As used herein, the term "acetone solution" refers to a solution in which the solvent comprises acetone. The acetone solution may also comprise other additives besides acetone.

The acetone solution may comprise a tin compound including, but not limited to, stannous bromide, stannous chloride, stannic chloride, stannic chloride dihydrate, stannic chloride pentahydrate, stannic chloride tetrahydrate, stannic chloride trihydrate, stannic chloride diamine, stannic trichloride bromide, stannic chromate, stannous fluoride, stannic fluoride, stannic iodide, stannic sulfate, stannic tartrate, stannous acetate, and the like compounds. In one embodiment, the acetone solution comprises stannic chloride dihydrate.

The support material may comprise silicon oxide, aluminum oxide, titanium oxide, zirconium oxide, carbon, magnesium oxide, calcium oxide, zinc oxide, cerium oxide, zeolite, or combinations thereof. In one embodiment, the support material is a silica gel.

As used herein, the term "silica gel" is intended to mean a silica compound having the formula of $SiO_2$. The silica gel may or may not be hydrated. The silica gel may have an average pore size in the range of 0 to 500 Angstroms. The silica gel may comprise mesoporous nanoparticles. In one embodiment, the silica gel comprises mesoporous silica SBA-15 nanoparticles. In another embodiment, the silica gel comprises mesoporous silica MCF-17 nanoparticles. Alternatively, the silica gel comprises mesoporous silica MCM-41 nanoparticles.

Methods of mixing a support material with one or more metals in a solution are well known in the art and include impregnation, incipient wetness, co-precipitation, precipitation-deposition, and chemical vapor deposition (see, e.g., Deng et al., Dehydrogenation of Propane over Silica-Supported Platinum-Tin Catalysts Prepared by Direct Reduction: Effects of Tin/Platinum Ratio and Reduction Temperature," *ChemCatChem* 6(9):2680-2691 (2014) and Bariåas et al., "Propane Dehydrogenation over Supported Pt and Pt—Sn Catalysts: Catalyst Preparation, Characterization, and Activity Measurements," *J. Catalysis* 158(1):1-12 (1996), which are hereby incorporated by reference in their entirety).

The metal-loaded support may be heated to a temperature of about 80° C. to dry the support material. In some embodiments, the metal-loaded support is stirred overnight until dried.

The catalyst comprising a metal-loaded support may be reduced in the presence of a reducing agent or hydrogen. In accordance with these embodiments, the metal-loaded support may be reduced at 30-1000° C. for up to 3 hours. In some embodiments, the metal-loaded support is reduced at about 250-500° C. for 1-2 hours.

The catalyst comprising a metal-loaded support is treated at a temperature of 50-500° C. for 1-2 hours. Alternatively, the catalyst is treated for up to 20 hours. A further alternative involves treating at 200-240° C.

The atmosphere for carrying out the treating may comprise saturated or unsaturated C1-C6 hydrocarbons, hydrogen, or combinations thereof. Exemplary atmospheres for carrying out the treating comprise any of the following: acetylene, ethylene, and hydrogen; acetylene and ethylene; ethylene; or acetylene.

In some embodiments, the one or more metals comprise platinum and tin. In accordance with this embodiment, the metal-containing catalyst is a platinum-tin catalyst. The platinum-tin catalyst may have a tin:platinum molar ratio of 0.01:1 to 2:1. For example, the platinum-tin catalyst may have a molar ratio of 0.3:1 or 1:1.

The present invention also relates to a catalytic agent, which comprises a support material and a platinum-containing catalyst supported on the support material. The platinum-containing catalyst is stable for 40-1000 hours at conditions suitable for the catalytic agent to convert propane to propylene.

As described above, the support material may comprise silicon oxide, aluminum oxide, titanium oxide, zirconium oxide, carbon, magnesium oxide, calcium oxide, zinc oxide, cerium oxide, zeolite, or combinations thereof. In one embodiment, the support material is a silica gel.

The platinum-containing catalyst may be a platinum-tin catalyst.

As used herein, the term "catalytic agent" or "catalyst" refers to a substance that accelerates the rate of a chemical reaction.

This process involves catalytic dehydrogenation which is a catalytic endothermic equilibrium reaction that involves removal of a hydrogen from a hydrocarbon. Here, catalytic dehydrogenation reactions are often used to convert propane to propylene.

Suitable catalytic agents have high activity, high selectivity, and high stability. As used herein, "catalytic activity" or "catalytic conversion" refer to a measure of the catalytic agent's ability to convert a reactant to a product under a specific set of reaction conditions (i.e., temperature, pressure, concentration). As used herein, "catalytic selectivity" refers to a measure of the catalytic agent's ability to convert a reactant to the desired product relative to the amount of reactant converted. As used herein, "catalytic stability" is a measure of a catalytic agent's rate of change in activity and selectivity over time.

The catalytic agent of the present invention desirably has approximately 27% activity, greater than 99% selectivity, and is stable for greater than 75 hours.

The present invention further describes a process for converting propane to propylene. The process involves converting propane to propylene in the presence of the treated platinum-containing catalysts of the present invention.

The present invention also discloses a process for converting propane to propylene. The process involves providing a platinum-containing catalyst on a support material; treating the platinum-tin catalyst on a support material with an atmosphere comprising 0.01 to 100% carbon-containing agents and 0-100% hydrogen at a temperature of 50 to 500° C. to produce a treated platinum-containing catalyst on a support material; and converting propane to propylene in the presence of the treated platinum-containing catalyst on a support.

Exemplary platinum-containing catalysts and support materials are described above.

The treatment phase of this process is carried out using the steps, reagents, and conditions fully described above.

As described above, the conversion of propane to propylene involves catalytic dehydrogenation, which is an endothermic process. The reaction is reversible and accompanied by volume expansion. Dehydrogenation reaction conditions include temperatures ranging from about 400° C. to about 900° C. and pressures from about 0.01 to 10 atmospheres. High reaction temperatures favor various side reactions such as thermal cracking to coke and light alkanes, which reduce product yield and increase catalyst deactivation. Several other dehydrogenation side reactions, including, but not limited to deep dehydrogenation, hydrogenolysis, and polymerization also impact the purity of the desired reaction products. The extent of these side reactions is controlled by the catalyst formulation and the operating conditions.

Various processes for converting propane to propylene using a dehydrogenation reactor are well known in the art. In some embodiments, a propane feed is introduced to a dehydrogenation reactor that contains a catalytic agent and is operating at dehydrogenating conditions to produce an effluent.

The dehydrogenation reactor may comprise one or more feed streams, including, but not limited to: a propane feed, a helium feed, a hydrogen feed, a recycled effluent feed, and combinations thereof. Each stream may be introduced into the endothermic dehydrogenation reactor at the same or different rates.

Suitable dehydrogenation reactors include, but are not limited to, a batch reactor, a stirred tank reactor, a continuous stirred tank reactor (CSTR), a tubular reactor, a shell-and-tube heat exchanger reactor, a multiple-pass reactor, a reactor having microchannels, a short contact time reactor, a catalytic fixed bed reactor, or a reactor having a combination of the foregoing features. A dehydrogenation reactor may include a single endothermic dehydrogenation zone or multiple endothermic dehydrogenation zones. The dehydrogenation reaction zones may be arranged as one or more of the following: a fixed bed, a fluidized bed, and spouted bed. All such configurations are well known in the art. Each reaction zone may optionally include one or more sub-zones, each of which may differ, for example, in operating temperature, catalyst composition, or catalyst concentration. In some embodiments, the process utilizes a plurality of reactor beds with heating elements placed between each reactor bed. In accordance with these embodiments, the reheating of the effluent from one reactor before passing to a subsequent reactor allows for continuous processing.

The effluent may contain propylene, unconverted propane, hydrogen, and various other hydrocarbons. The effluent may be cooled and separated to form a propylene product stream and a propane-rich recycle stream, which may be introduced to the dehydrogenation reactor along with additional fresh propane feed.

EXAMPLES

Example 1

Synthesis of 1% PT/$SiO_2$ Catalysts

1% Pt/$SiO_2$ was prepared by impregnating the $SiO_2$ support with an adequate volume of aqueous $H_2PtCl_6 \cdot 6H_2O$ (1 wt % Pt). $H_2PtCl_6 \cdot 6H_2O$ (116 mg, 0.256 mmol) was dissolved in deionized water (100 mL) in a conical flask. Silica gel (5 g) was added. The solution was stirred at 80° C. overnight until dried. The sample was stored in the dark in a desiccator until further use.

Example 2

Synthesis of 1% Pt—Sn/$SiO_2$ (Sn/Pt=1, Molar Ratio)

$SnCl_2 \cdot 2H_2O$ (5.8 mg) was dissolved in 25 mL acetone in a conical flask. Dried 1 wt % Pt/$SiO_2$ catalyst (0.5 g) was added to the flask. The solution was stirred at 80° C. overnight until dried. The sample was stored in the dark in a desiccator until further use. The catalyst was reduced at 500° C. for 1 h prior to use in a catalytic test.

Example 3

Synthesis of Other PtSn Catalysts

Additional PtSn catalysts that are similar to the 1% PtSn/$SiO_2$ catalyst were prepared. SBA-15, MCM-41, or MCF-17 were used in place of silica gel. Appropriate amounts of Pt or Sn precursors were used for the samples with various Pt loading or Sn/Pt molar ratio.

Example 4

Treatment of Catalyst

The treatment of catalysts was carried out using appropriate agents containing carbon, such as acetylene or ethylene, as the carbon source. In typical conditions, the sample was treated using a gaseous mixture composed of 13.5 mL/min He (99.999%), 1.5 mL/min $H_2$ (99.995%), 15 mL/min $C_2H_4$ (99.9%), 0.15 mL/min $C_2H_2$ (99.9%) at 240° C. for 2 h. The treatment was also carried out using only He/$H_2$/$C_2H_4$ or He/$H_2$/$C_2H_2$.

Example 5

Catalytic Test

The dehydrogenation of propane was carried out in a fritted quartz U-tube reactor. Typically 30 mg catalyst was weighed and mixed with 2.0 g quartz sands. The reaction gases were composed of 5.6 mL/min He (99.999%), 2.8 mL/min $H_2$ (99.995%), 2.8 mL/min $C_3H_8$ (99.9%) at 1 bar. The gas composition was monitored on line by a HP 5890 gas chromatograph equipped with a capillary column (HP PLOT Q, 30 m×0.25 mm×0.25 μm) with a flame ionization detector.

Example 6

Influence of Treatment: Silica Gel as the Support 30 mg of silica gel supported PtSn catalyst (1% PtSn/$SiO_2$, Sn/Pt=1, in molar ratio) was tested in the dehydrogenation of propane. The performance of the catalyst with or without treatment is shown in Table 1.

TABLE 1

Catalytic Performance of 1% PtSn/SiO$_2$ With or Without Treatment

|  | Catalyst without treatment | Catalyst with treatment using ethylene and acetylene |
|---|---|---|
| Conversion, initial (%) | 19.5 | 23.3 |
| Selectivity, initial (%) | 99.5 | 98.7 |
| Conversion, 10 h (%) | 16.4 | 23.3 |
| Selectivity, 10 h (%) | 99.6 | 99.1 |
| Change in conversion (%) | −3.1 | 0 |
| Change in selectivity (%) | +0.1 | +0.4 |

Figure 2:
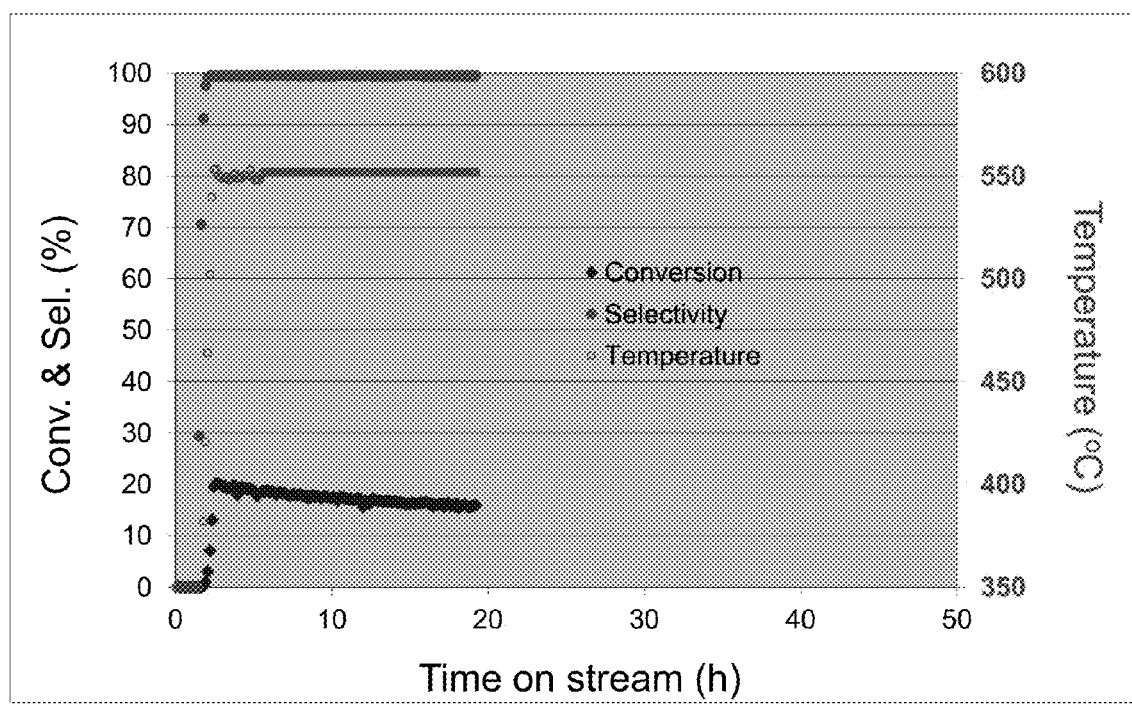
FIG. 2 is a graph showing the conversion and selectivity of the catalytic dehydrogenation of propane to propylene using an untreated 1% $PtSn/SiO_2$ catalyst.

Without treatment, PtSn/SiO$_2$ catalyst showed a conversion of 19.5% at the beginning of the test at 550° C. This catalyst deactivated quickly after a 10 hour run (16.4% conversion). After the treatment with the mixture comprising of acetylene, ethylene, hydrogen, and helium, the catalyst showed 23.3% conversion at the beginning and maintained the activity after 10 h, indicating that the stability of the catalyst was significantly improved. The selectivity to propylene is kept at approximately 99%. The time dependent performance of the catalyst is shown in FIGS. 1 and 2.

Example 7

Influence of Treatment: SBA-15 Mesoporous Silica as the Support 30 mg of mesoporous silica SBA-15 supported PtSn catalyst (1% PtSn/SBA-15, Sn/Pt=1, in molar ratio) was tested for the dehydrogenation of propane. The performance of the catalyst is shown in Table 2.

TABLE 2

Catalytic Performance of 1% PtSn/SBA-15 With or Without Treatment

|  | Catalyst without treatment | Catalyst with treatment | Catalyst with treatment using ethylene and acetylene | Catalyst with treatment using ethylene |
|---|---|---|---|---|
| Conversion, initial (%) | 21.5 | 23.9 | 22.2 | 21.9 |
| Selectivity, initial (%) | 96.9 | 99.0 | 99.5 | 99.1 |
| Conversion, 20 h (%) | 21.2 | 23.2 | 21.3 | 21.2 |
| Selectivity, 20 h (%) | 98.8 | 99.4 | 99.6 | 99.5 |
| Change in conversion (%) | −0.3 | −0.7 | −0.9 | −0.7 |
| Change in selectivity (%) | +1.9 | +0.4 | +0.1 | +0.4 |

All catalysts showed good stability in terms of conversion. Without treatment, PtSn/SBA-15 catalyst has a 96.9% at the beginning and 98.8% after 20 h. Improved selectivity (99.0-99.6%) could be obtained after the treatment using either ethylene, acetylene or ethylene and acetylene.

Example 8

Influence of Treatment: MCF-17 Mesoporous Silica as the Support 30 mg of mesoporous silica MCF-17 supported PtSn catalyst (1% PtSn/MCF-17, Sn/Pt=1, in molar ratio) was tested for the dehydrogenation of propane. The performance of the catalyst is shown in Table 3.

TABLE 3

Catalytic Performance of 1% PtSn/MCF-17 With or Without Treatment

|  | Catalyst without treatment | Catalyst with treatment |
|---|---|---|
| Conversion, initial (%) | 21.0 | 23.1 |
| Selectivity, initial (%) | 99.5 | 99.3 |
| Conversion, 20 h (%) | 17.2 | 21.9 |
| Selectivity, 20 h (%) | 99.7 | 99.5 |
| Change in conversion (%) | −3.8 | −1.2 |
| Change in selectivity (%) | +0.2 | +0.2 |

Without treatment, PtSn/MCF-17 catalyst showed 21.0% conversion at the beginning, and deactivated quickly after 20 h (17.2%). After treatment using acetylene, the catalyst showed 23.1% conversion at the beginning, and 21.9% conversion after 20 h, indicating the stability of catalyst was significantly improved after the treatment.

Example 9

Influence of Treatment Temperature 30 mg of mesoporous silica SBA-15 supported PtSn catalyst (1% PtSn/SBA-15, Sn/Pt=1, in molar ratio) was tested for the dehydrogenation of propane. The catalyst was treated with acetylene at various temperatures (240, 300, 500° C.) for 2 h. The performance of the catalyst is shown in Table 4.

TABLE 4

Catalytic performance of 1% PtSn/SBA-15 with treatment at various temperatures

|  | Catalyst with treatment at 240° C. | Catalyst with treatment at 300° C. | Catalyst with treatment at 550° C. |
|---|---|---|---|
| Conversion, initial (%) | 23.9 | 20.5 | 8.2 |
| Selectivity, initial (%) | 99.0 | 99.2 | 99.2 |
| Conversion, 20 h (%) | 23.2 | 18.3 | 9.2 |
| Selectivity, 20 h (%) | 99.4 | 99.5 | 99.3 |
| Change in conversion (%) | −0.7 | −2.2 | +1.0 |
| Change in selectivity (%) | +0.4 | +0.3 | +0.1 |

All catalysts showed good stability during the test. However, the activity decreased greatly when higher temperature was used during the treatment. The catalyst treated at 240° C. showed the highest conversion: 23.9% at the beginning and 23.2% after 20 h.

Example 10

Influence of Sn/Pt Ratio 30 mg of mesoporous silica SBA-15 supported PtSn catalyst (1% PtSn/SBA-15; Sn/Pt=0, 0.1, 0.33, 0.5, 0.8, 1.0, 1.2 or 2.0, in molar ratio) was tested for the dehydrogenation of propane. The catalyst was treated with acetylene at 240° C. for 2 h. The performance of the catalyst is shown in Table 5.

TABLE 5

Catalytic Performance of 1% PtSn/SBA-15 with Various Sn/Pt

| | Sn/Pt = 0 | Sn/Pt = 0.3 | Sn/Pt = 0.5 | Sn/Pt = 0.8 | Sn/Pt = 1.0 | Sn/Pt = 1.2 | Sn/Pt = 2.0 |
|---|---|---|---|---|---|---|---|
| Conversion, initial (%) | 40 | 23.1 | 22.2 | 18.5 | 23.9 | 14.5 | 16.4 |
| Selectivity, initial (%) | 35 | 98.2 | 98.8 | 99.4 | 99.0 | 99.4 | 99.4 |
| Conversion, 20 h (%) | 24 | 22.2 | 20.1 | 16.8 | 23.2 | 11.7 | 15.3 |
| Selectivity, 20 h (%) | 68 | 99.2 | 99.6 | 99.5 | 99.4 | 99.4 | 99.6 |
| Change in conversion (%) | −36 | −0.9 | −2.1 | −1.7 | −0.7 | −2.8 | −1.1 |
| Change in selectivity (%) | +31 | +1.0 | +0.8 | +0.1 | +0.4 | 0 | +0.2 |

The results show that excellent stability, activity, and selectivity can be achieved on the catalyst at various Sn/Pt ratios, including, but not limited to, Sn/Pt=0.3 or 1.0.

Example 11

Influence of Pt Loading Amount (I)

Appropriate amount of mesoporous silica SBA-15 supported PtSn catalyst containing 0.1% Pt, 1% Pt, or 3% Pt (Sn/Pt=1.0, molar ratio), was tested for the dehydrogenation of propane. The catalyst was treated with acetylene at 240° C. for 2 h. The performance of the catalyst is shown in Table 6.

TABLE 6

Catalytic Performance of PtSn/SBA-15 with Various Pt Loading

| | 0.1% Pt | 1% Pt | 3% Pt |
|---|---|---|---|
| Conversion, initial (%) | 18.9 | 23.9 | 21.8 |
| Selectivity, initial (%) | 99.1 | 99.0 | 98.9 |
| Conversion, 20 h (%) | 16.6 | 23.2 | 21.3 |
| Selectivity, 20 h (%) | 99.5 | 99.4 | 99.4 |
| Change in conversion (%) | −2.3 | −0.7 | −0.5 |
| Change in selectivity (%) | +0.4 | +0.4 | +0.5 |

The results showed that optimal performance in terms of stability, activity, and selectivity can be achieved using appropriate Pt loading amount such as 1-3% Pt.

Example 12

Influence of Pt Loading Amount (II)

Appropriate amount of mesoporous silica MCF-17 supported PtSn catalyst containing 1% Pt, 5% Pt, or 10% Pt (Sn/Pt=1.0, molar ratio), was tested for the dehydrogenation of propane. The catalyst was treated with acetylene at 240° C. for 2 h. The performance of the catalyst is shown in Table 7.

TABLE 7

Catalytic Performance of PtSn/MCF-17 with Various Pt Loading

| | 1% Pt | 5% Pt | 10% Pt |
|---|---|---|---|
| Conversion, initial (%) | 23.1 | 9.7 | 8.2 |
| Selectivity, initial (%) | 99.3 | 99.3 | 99.3 |
| Conversion, 20 h (%) | 21.9 | 6.4 | 4.5 |
| Selectivity, 20 h (%) | 99.5 | 98.9 | 98.9 |
| Change in conversion (%) | −1.2 | −3.3 | −3.7 |
| Change in selectivity (%) | +0.2 | −0.4 | −0.4 |

The results showed that excellent stability, activity and selectivity can be only obtained on catalyst with appropriate Pt loading amount such as 1% Pt.

Example 13

Long-term Stability Test (I)

Figure 3:
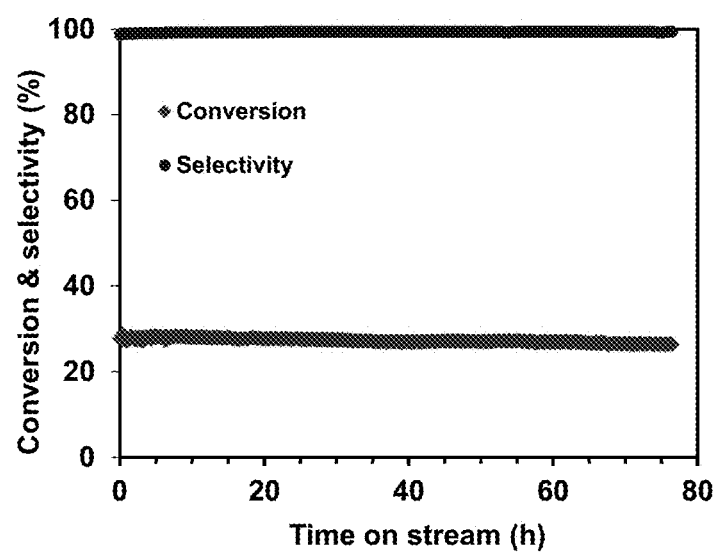
FIG. 3 is a graph showing the results of a long-term stability test of a silica gel supported PtSn catalyst treated with acetylene at 240° C. for two hours. 73 mg of the 1% $PtSn/SiO_2$ acetylene-treated catalyst was used to dehydrogenate propane in a catalytic test in the presence of $He/H_2/C_3H_8$=5.6/2.8/2.8 mL/min at 550° C.

73 mg of silica gel ($SiO_2$) supported PtSn catalyst (1% PtSn/$SiO_2$; Sn/Pt=1.0, in molar ratio) was tested for the dehydrogenation of propane. The catalyst was treated with acetylene at 240° C. for 2 h. The time dependent performance of the catalyst is shown in FIG. 3. 27.8% conversion and 99.0% selectivity to propylene were obtained at 550° C. at the beginning of the reaction. After 75 h, the conversion dropped to 26.5%, while the selectivity was maintained at 99.4%.

Example 14

Long-term Stability Test (II)

Figure 4:
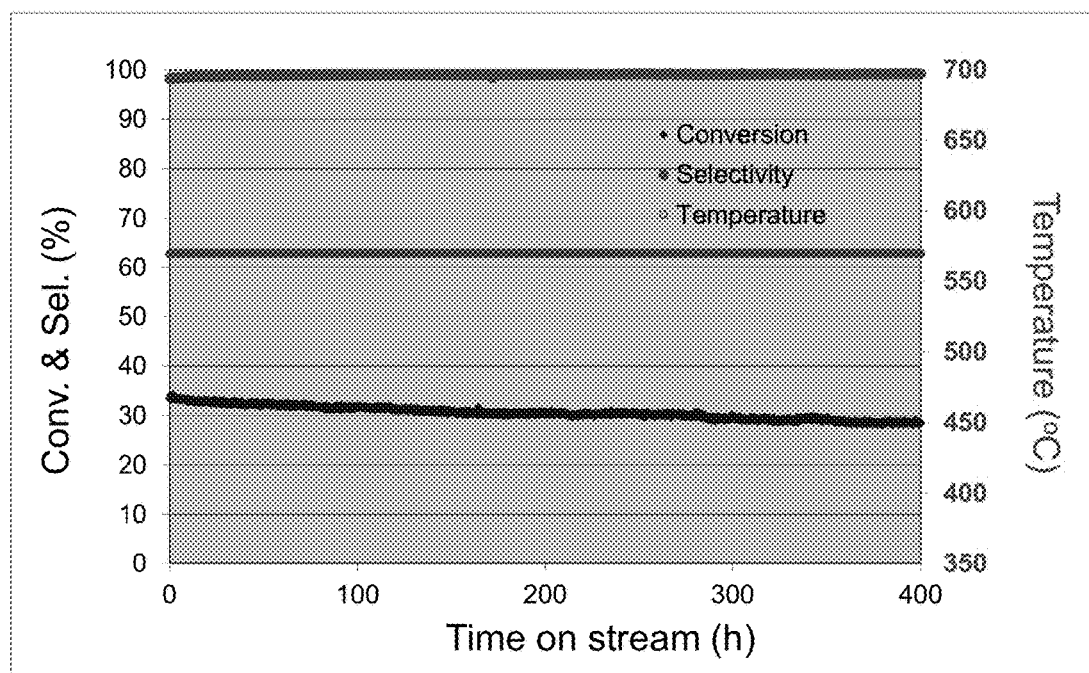
FIG. 4 is a graph showing the results of a long-term stability test of a mesoporous silica SBA-15 supported PtSn catalyst treated with acetylene at 240° C. for two hours. 120 mg of the 1% PtSn/SBA-15 catalyst was used to dehydrogenate propane in a catalytic test in the presence of $He/H_2/C_3H_8$=5.6/2.8/2.8 mL/min. The reaction was conducted after reduction in the flow of $He/H_2/C_2H_2$=13.5/1.5/0.15 mL/min at 570° C.

120 mg of mesoporous silica SBA-15 supported PtSn catalyst (1% PtSn/SBA-15; Sn/Pt=1.0, molar ratio) was tested for the dehydrogenation of propane. The catalyst was treated with acetylene at 240° C. for 2 h. The time dependent performance of the catalyst is shown in FIG. 4. 33.4% conversion and 98.2% selectivity to propylene were obtained at 570° C. at the beginning of the reaction. After 400 h, the conversion dropped to 28.6%, while the selectivity was maintained at 99.2%.

Example 15

Characterization of $PtSn/SiO_2$

Figure 5:
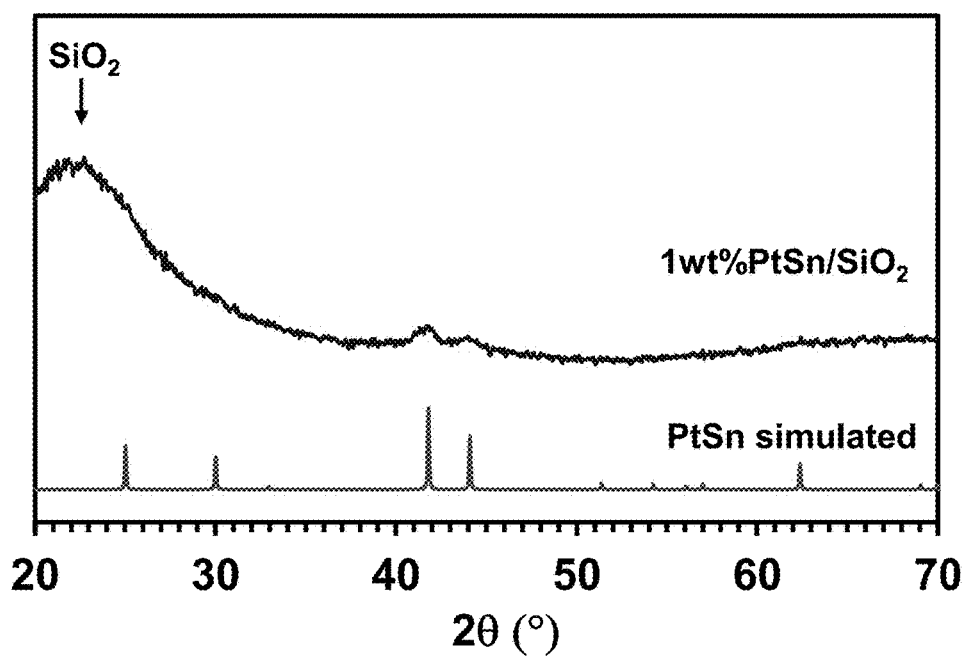
FIG. 5 shows the powder X-ray diffraction pattern of a 1% $PtSn/SiO_2$ catalyst.

FIG. 5 shows a powder X-ray diffraction (XRD) pattern of 1% $PtSn/SiO_2$ catalyst. The sample mainly comprises PtSn intermetallic phase. The average crystalline size of PtSn is calculated to be 6.6±1.1 nm, according to the Scherrer equation.

Example 16

Characterization of PtSn/SBA-15

Figure 6:
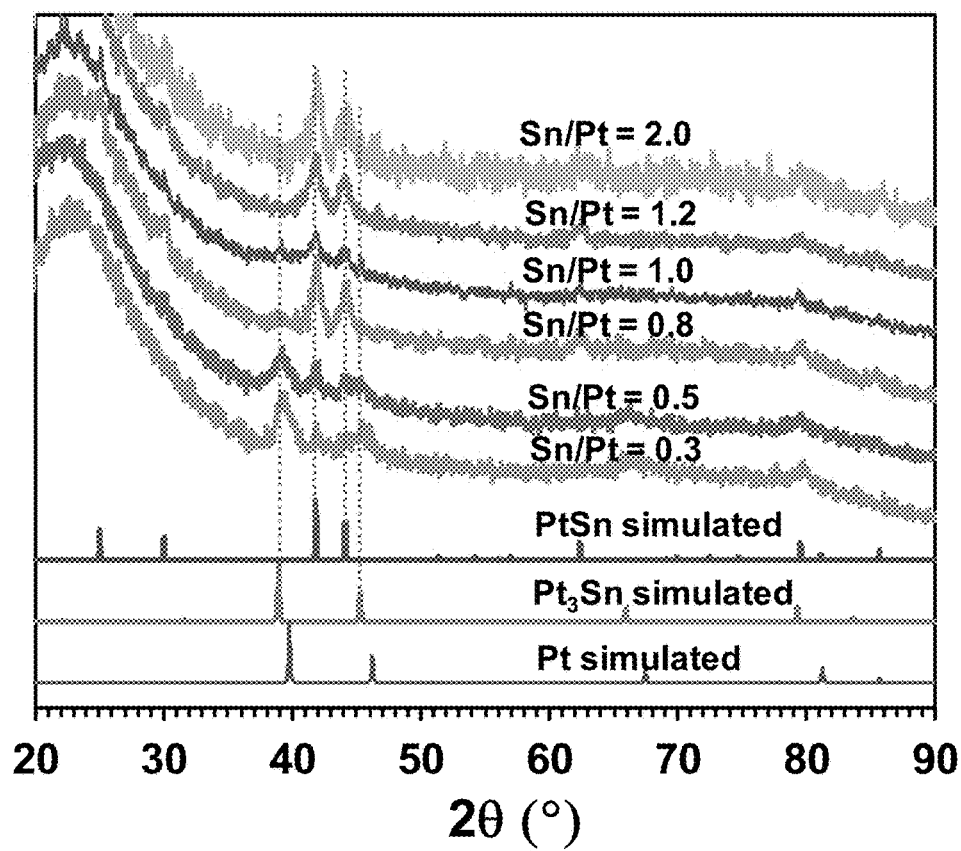
FIG. 6 shows the powder X-ray diffraction pattern of 1% PtSn/SBA-15 catalysts with various Sn/Pt molar ratios.

FIG. 6 shows a powder X-ray diffraction (XRD) pattern of 1% PtSn/SBA-15 catalyst with various Sn/Pt ratio. The samples mainly consist of $Pt_3Sn$ and/or PtSn intermetallic phases. Among all catalyst, $Pt_3Sn$ phase is the main phase at Sn/Pt=0.3. However, PtSn phase is predominant at Sn/Pt=1.

Example 17

TEM Picture of PtSn/SBA-15

Figure 7:
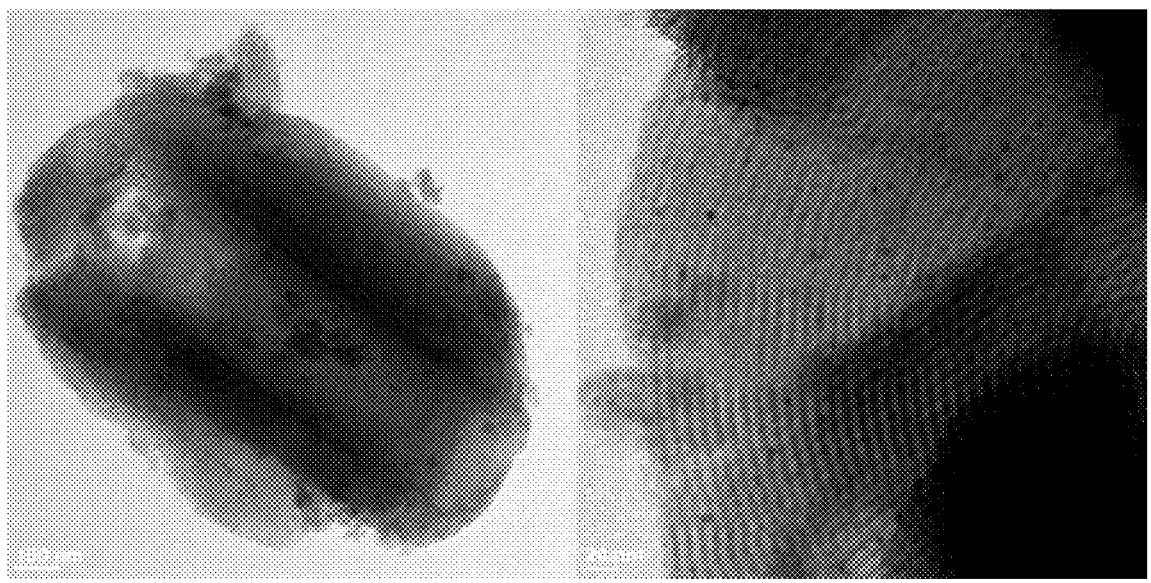
FIG. 7 is a transmission electron microscopy image of 1% PtSn/SBA-15 (Sn/Pt=1) particles.

TEM images of 1% PtSn/SBA-15 are shown in FIG. 7. PtSn particles are uniformly dispersed in pores of SBA-15 support. No agglomeration was found. The average particle size of PtSn is approximately 6 nm.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A process of producing a platinum-tin catalyst, said process comprising:
    mixing a support material with platinum and tin compounds in a solution to produce a catalyst comprising a platinum and tin-loaded support;
    reducing the catalyst comprising the platinum and tin-loaded support in the presence of a reducing agent; and
    treating the reduced catalyst in a gaseous atmosphere comprising 0.01 to 100% carbon-containing agents and 0-100% hydrogen at a temperature of 50 to 500° C. to produce a treated platinum-tin catalyst.

2. A process of producing a platinum-tin catalyst, said process comprising:
    mixing a support material with platinum and tin compounds in a solution to produce a catalyst comprising a platinum and tin-loaded support;
    reducing the catalyst comprising the platinum and tin-loaded support in the presence of hydrogen; and
    treating the reduced catalyst in a gaseous atmosphere comprising 0.01 to 100% carbon-containing agents and 0-100% hydrogen at a temperature of 50 to 500° C. to produce a treated platinum-tin catalyst.

\* \* \* \* \*